(12) United States Patent
Besoyan

(10) Patent No.: US 6,682,511 B2
(45) Date of Patent: Jan. 27, 2004

(54) BRIEF PROTECTOR

(76) Inventor: Robert Wallace Besoyan, 18627 Brookhurst St., #394, Fountain Valley, CA (US) 92708

( * ) Notice: Subject to any disclaimer, the term of this patent is extended or adjusted under 35 U.S.C. 154(b) by 0 days.

(21) Appl. No.: 10/081,471

(22) Filed: Feb. 21, 2002

(65) Prior Publication Data

US 2003/0204176 A1 Oct. 30, 2003

(51) Int. Cl.⁷ .................................................. A61F 5/44
(52) U.S. Cl. ........................................................ 604/353
(58) Field of Search ................................. 604/317, 327, 604/346, 347, 349–351, 353, 355

(56) References Cited

U.S. PATENT DOCUMENTS

| | | |
|---|---|---|
| 1,229,423 A | 6/1917 | Eckenrode |
| 1,372,101 A | 3/1921 | Snow |
| 1,490,793 A | 4/1924 | Ajamian et al. |
| 3,032,038 A | 5/1962 | Swinn |
| 3,298,370 A | 1/1967 | Beatty |
| 3,526,227 A | 9/1970 | Appelbaum |
| 3,559,651 A | 2/1971 | Moss |
| 3,721,243 A | 3/1973 | Hesterman et al. |
| 4,022,213 A | 5/1977 | Stein |
| 4,387,726 A | 6/1983 | Denard |
| 4,521,213 A | 6/1985 | Steigerwald |
| 4,673,401 A | 6/1987 | Jensen et al. |
| 4,846,816 A | 7/1989 | Manfredi |
| 5,009,649 A | 4/1991 | Goultier et al. |
| 5,423,785 A | 6/1995 | Hart |
| 5,618,277 A | 4/1997 | Goultier |
| 5,645,541 A | 7/1997 | Bouser |
| 5,921,914 A | 7/1999 | Tucker et al. |
| 5,935,116 A | 8/1999 | Kristensen |
| 6,045,542 A * | 4/2000 | Cawood ...................... 604/327 |
| 6,336,920 B1 * | 1/2002 | Temple ........................ 604/355 |

* cited by examiner

*Primary Examiner*—Weilun Lo
*Assistant Examiner*—Michael G. Bogart
(74) *Attorney, Agent, or Firm*—Orrick, Herrington & Sutcliff LLP

(57) ABSTRACT

There is disclosed herein a male incontinence device comprising a form of brief having a waistband adapted to be worn around the waist of a male wearer, a reservoir assembly having an upper end securely attached to the waistband, and a penis condom having an upper end portion. The incontinence device includes a unique quick release and locking mechanism for the upper end of the penis condom to allow the same to be firmly attached to any size penis of a wearer of the device. The penis condom has a lower opening communicating via an anti-siphon valve with the reservoir. A drain assembly is coupled with the lower end of the reservoir to allow selective drainage of the reservoir, and the drain assembly has one or more fluid locking devices, to lock the drain assembly and prevent accidental drainage of the urine reservoir.

25 Claims, 4 Drawing Sheets

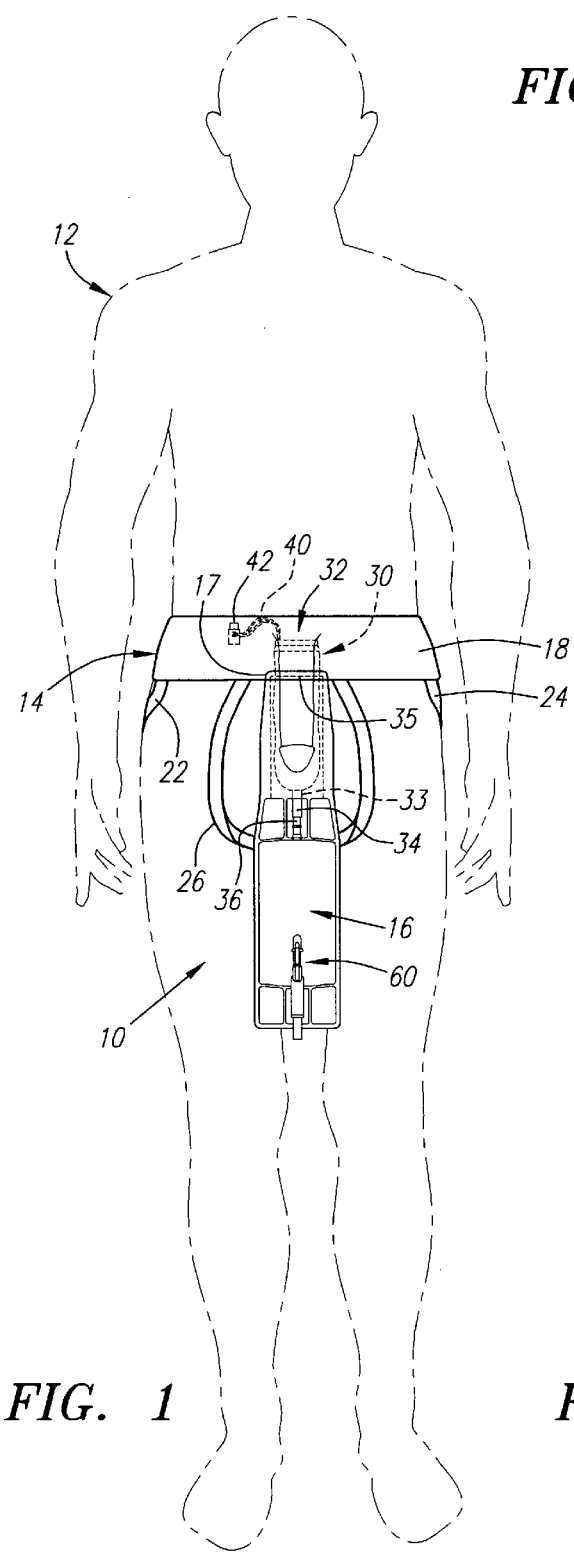
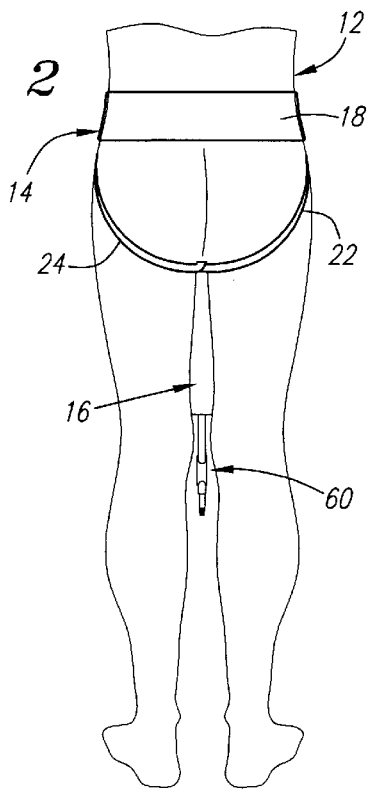
FIG. 1
FIG. 2
FIG. 3

BRIEF PROTECTOR

The present invention relates to male incontinence devices, and more particularly to a self-contained, one unit reusable device, that is comfortable, easy to utilize, economical and designed with a simple unique quick release and locking draw string mechanism. This new mechanism allows any size or shape penis, to enter the penis condom easily and securely, one size fits all men. This device has completely eliminated the major common problem of previous similar devices, where the condom easily comes off of the male penis, causing major urine spillage, embarrassment and humiliation to the user.

BACKGROUND OF THE INVENTION

There are numerous situations in which male incontinence can become a problem. Many incontinent conditions occur due to illness, accidents, cancer, birth defects, mental problems, etc. Prostate cancer is one of the major reasons male incontinence is increasing each year throughout the World, in the United States alone it is estimated there are over 400,000 men yearly that are diagnosed with this disease. Latest statistics indicate there are over 10 million American men that are incontinent, but less then 10% of those who suffer from it seek medical attention. It also has been calculated that American's spend billions of dollars a year, in the quest to stay dry 24 hours a day.

Bedwetting, leakage, dribbling and the like are many names for incontinence or loss or urinary control. Incontinence can occur, for example, for a number of reasons including age and physical stress, such as even from heavy lifting. Treatment for prostate cancer, such as radical prostatectomy and radiation therapy also can lead to severe incontinence. Among men who undergo surgery for prostate cancer, in many cases the condition is temporary and resolves itself over time or can be corrected with minor treatment. However, a number of radical prostatectomy patients experience severe incontinence, because the external sphincter was destroyed or made dysfunctional, by extensive surgery to remove all of the cancer that was present in the patient.

Numerous attempts have been made to obviate the aforementioned problems, and examples are found in the devices disclosed in a number of U.S. Patents including U.S. Pat. No. 1,490,793 issued in 1924, U.S. Pat. No. 4,022,213 issued in 1997, and U.S. Pat. No. 5,618,277 issued in 1997, and which patents also evidence the attempts over a substantial period of time to address and/or solve this problem. Many of the prior devices have shortcomings of one form or another. These include bulky and uncomfortable devices, difficult to use, with small urine storage capacity, requiring the user to empty their urine reservoir several times during the daytime and nighttime hours, making it impossible to get a good nights sleep. These devices must be removed to enable defecation, the requirement of various size penis condoms, the provision of multiple components that must be used together, cumbersome and difficult to use attachment arrangements, and importantly the provision of suitable support for the weight of the device along with the collected urine without placing great stress on the body and particularly on the penis.

SUMMARY OF THE INVENTION

The present invention provides a unique self-contained, one unit reusable incontinent device, similar in size to a man's boxer shorts. Urine capacity is 36.7 fluid ounces or 1100 ccs, sufficient for 24 hours of continuous usage without emptying. This device requires no catheterization or adhesive, to hold the penis comfortably in one position, due primarily to a novel quick release and locking drawstring mechanism. This new mechanism allows any size or shape penis, to enter the penis condom easily and securely, one size fits all men. This device, may be utilized both awake or asleep, with total confidence, anytime or place. The user may defecate anytime without having to remove this device. Due to a unique weight bearing feature, created by heavy-duty construction and design, allows the weight of the device and its contents, to be distributed to the users waist, thighs and hips. There is no weight bearing required by the penis, with this new approach. This self-contained device, has everything provided in one small area, there are no attachments required. The device does not require; hooks, rings, adhesive strips, glue, buzzer sounds, snap fasteners, latches, strands, straps, Velcro, etc.

Accordingly, a principal object of the present invention is to provide an improved male incontinence device.

Another object of the present invention is to provide a male incontinence device that effectively meets the users needs, with total ease of operation and economical in expense.

BRIEF DESCRIPTION OF THE DRAWINGS

These and other objects and features of the present invention will become better understood through a consideration of the following description, taken in conjunction with the drawings in which:

FIG. 1 illustrates an exemplary device according to the present invention as worn by an adult male (shown in dashed lines), the device is in the storage position, FIG. 2 is a partial rear view thereof, the device is in the drain position, FIG. 3 is a partial side view illustrating how a reservoir of the present device can be maintained and concealed within a man's pants (in dashed lines), the device is in the drain position.

DETAILED DESCRIPTION

Figure 4:
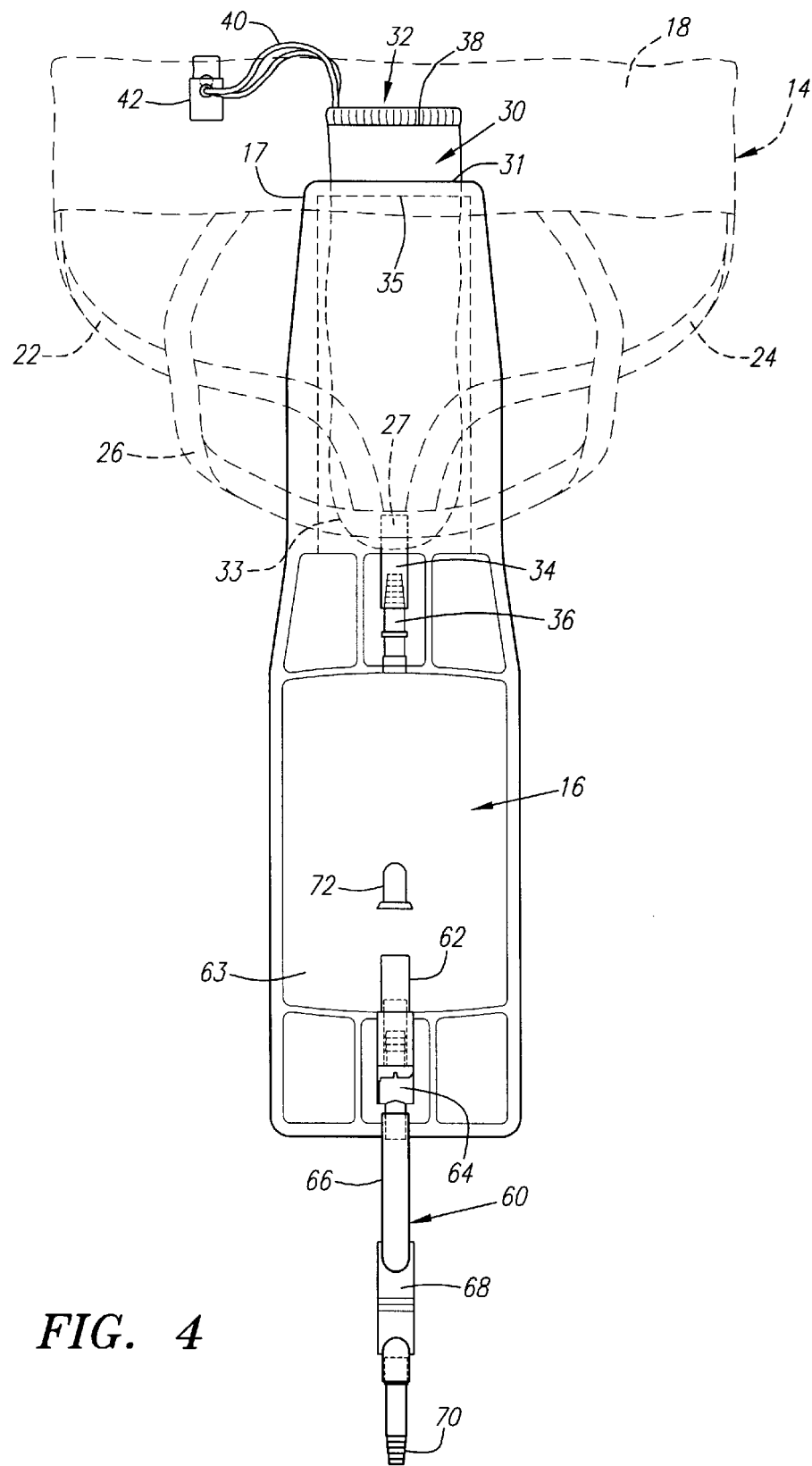
FIG. 4 is a more detailed view of the device of the present invention, the device is in the drain position.

Turning now to the drawings, and first to FIGS. 1 through 4, an incontinence device 10 according to the present invention is shown being worn by an adult male 12, who is shown in dashed lines. The device includes a heavy duty, stretchable cotton brief 14, unitary urine reservoir 16 having an upper end, attached to a waistband 18 of the brief 14. The reservoir 16 preferably is one unitary unit. The brief further includes a pair of support straps 22 and 24 and a support loop 26 attached at 27 (see FIG. 4) to ends of the straps 22 and 24. The upper ends of the straps 22 and 24 are attached to the lower side of the band 18 at the right and left sides thereof as seen in FIG. 1 and in dashed lines in FIG. 4, and the loop 26 likewise is attached to the front of the band 18. The lower ends of the straps 22 and 24 extend forwardly between the legs of the male and there are attached to the lower front ends of the straps 22 and 24 (near the male's abdomen) as shown in FIG. 1 and in dashed lines in FIG. 4. With the configuration of the straps 22 and 24 and the loop 26 as shown in the figures, there is no need to remove the present incontinence device 10 during defecation, as shown in FIG. 2.

The exemplary embodiment of the present incontinence device includes a penis condom 30, having a drawstring and quick-release locking mechanism 32 at the upper end thereof, thus allowing one size fits all men possible. The lower end 33 of the condom 30 has an anti-siphon valve 34 (note the enlarged view in FIG. 4 and the side view in FIG. 5), with an outlet coupled to a tube 36 affixed to the reservoir 16. The anti-siphon valve 34 prevents back flow of urine from the reservoir 16 into the condom 30. The condom 30 is only attached at the lower end 33.

The cotton brief 14, and particularly the band 18 thereof, supports the weight of the entire incontinence device including particularly the reservoir 16 and the condom 30. No weight is carried by the condom or penis. A drawstring and locking device 32 includes an upper hollow band 38 around the circumference of the upper end of the condom 30 within which a drawstring 40 is disposed. The upper end of the condom 30 thereby can be suitably cinched reasonably tight by pulling the drawstring 40 through the locking device 42 to prevent the penis from withdrawing from the condom 30 during use of the present incontinence device, this unique mechanism allows any size and shape penis to fit easily, comfortably and securely, in one position, with total confidence, 24 hours a day.

A typical size for the condom is 2½ inches wide and 7 inches long to accommodate all or virtually all males. It preferably is formed of Latex rubber and/or other materials. The condom 30 itself is not attached to the brief 14. The upper end of the condom sheath 17 of the reservoir 16 is stitched at 35 to the inside of the belt 18 of the brief 14 as shown in FIG. 4. This arrangement allows the brief, and particularly the band 18, to support the condom sheath 17 and the reservoir 16 (as well as the other components of the device for allowing drainage of the reservoir 16 as will be discussed below) and to support all of the weight of the device, particularly the reservoir 16 and the variable urine contents to be deposited therein through use of the present device.

Figures 5, 6:
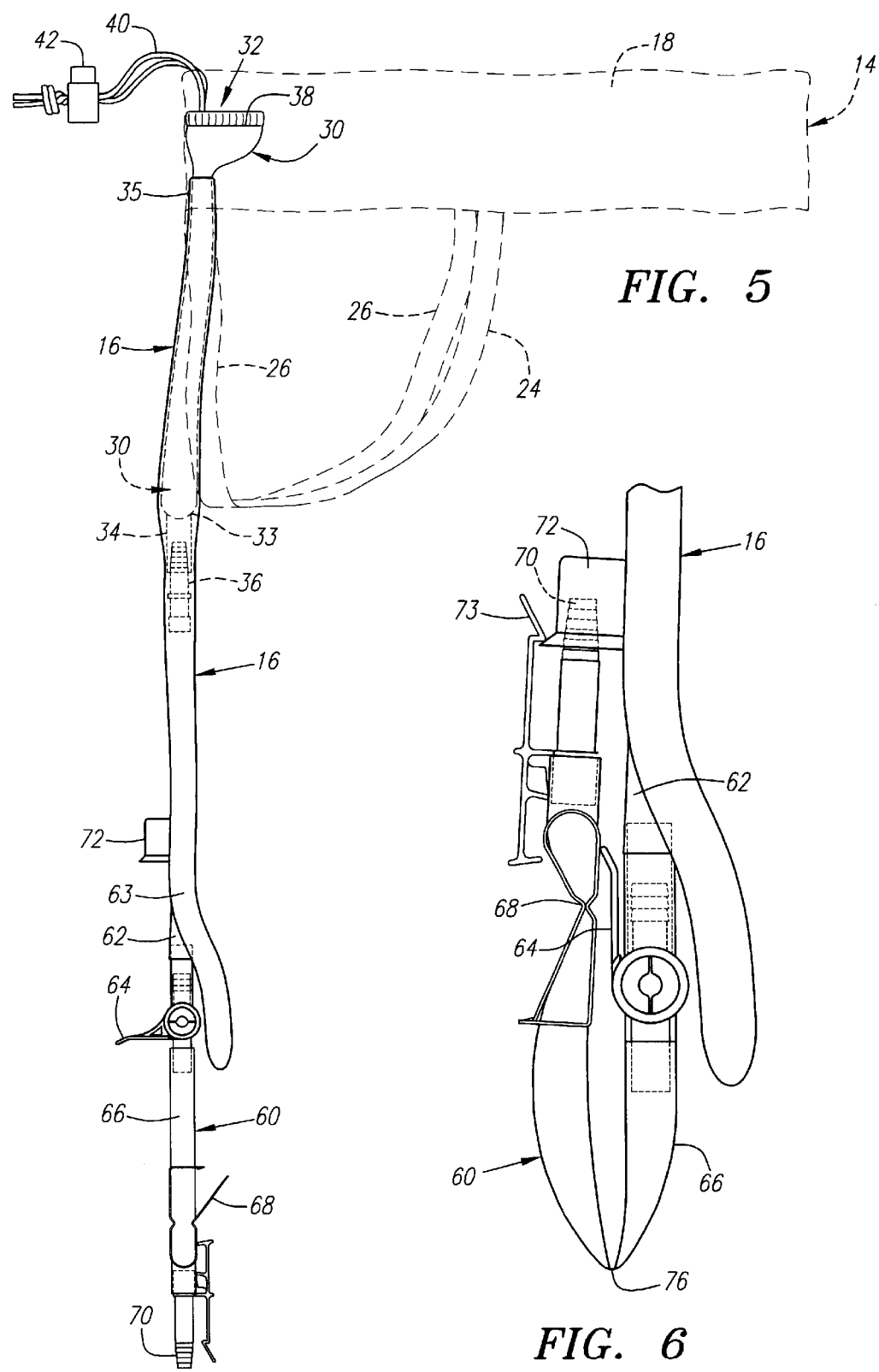
FIG. 5 is a side view of the device of the present invention before use particularly illustrating details of a condom and its attachment system for the penis, as well as the reservoir and drain mechanism of the device, the device is in the drain position.
FIG. 6 illustrates a secure storage position of the drain system of the device, FIG. 7 further illustrates the method of attachment of the condom device to a penis.
Figure 7:
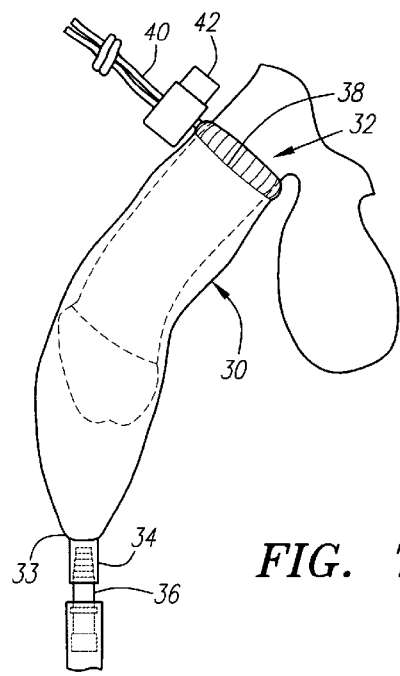
Figure 8:
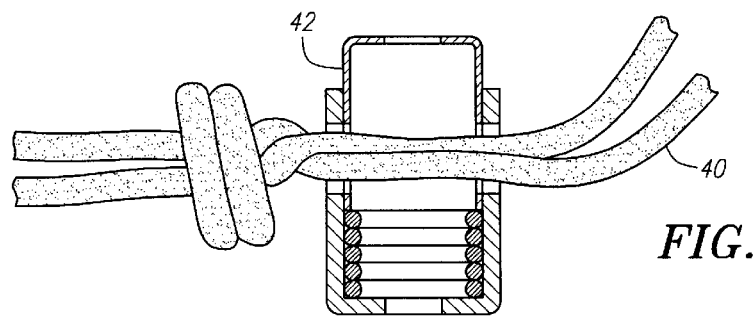
FIGS. 8 and 9 illustrate a device for easy release, adjustment and cinching of a drawstring of the condom.
Figure 9:
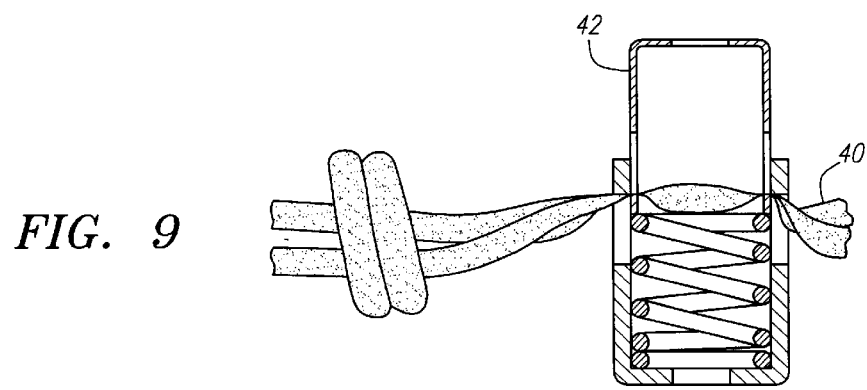

As will be appreciated, the reservoir 16 as it becomes full or otherwise contains urine will need to be drained. Accordingly, a suitable drain assembly 60 is provided which includes a tube or outlet 62 at the lower end 63 of the reservoir 16. A rotary valve 64 (shown open, FIG. 5) is connected with the tube 62 to provide a first shut-off, and extends to a lower tube 66, having a second click locking device 68 (shown open in FIG. 5). A novel universal adapter connector 70 preferably is connected to the lower end of the tube 66, and a receptacle 72 having an open lower end is affixed to the side of the reservoir 16 as best seen in FIGS. 5 and 6. The universal adapter connector can readily fit into a large capacity hospital urine container, when a user of the device becomes bed ridden because of illness, accident, or surgery, for an extended period of time.

The combination of the universal adapter 70 and receptacle 72 allows a further safety feature in the form of a "crimp lock" in tube 66 as indicated at 76 when the tube 66 and adapter 70 are folded up and the adapter 70 end is attached to the receptacle 72 via a locking mechanism 73 as illustrated in FIG. 6. Thus, three liquid locking devices are provided in the drain assembly 60, namely the rotary valve 64 (shown closed in FIG. 6), click lock 68 (shown closed in FIG. 6) and crimp lock 76. The drain assembly 60, and particularly the tube 66 thereof, is designed to be long enough so that the male user can easily unlock the three locks to lower the end of the adapter 70, so as to drain the reservoir 16 to a suitable container. FIG. 3 illustrates a typical length for the overall device to facilitate such draining conveniently. The arrangement of the adapter 70 and receptacle 72 also allows the drain assembly to be folded in a compact storage manner within the user's pants leg so as to be less obtrusive.

Features of the present device include the following:

The penis condom 30 is of a size and configuration that allows any sizes or shape, male penis to enter easily and comfortably.

The quick release and locking mechanism 32 allows the penis to be held in one position securely without discomfort.

The urine capacity of the reservoir 16 preferably is 1100 ccs or 36.7 ounces which is sufficient for 24 hours of continuous usage without emptying. Thus, the user will not need to be awakened during the night in order to stay dry. Current devices require the user to be awakened a couple of times nightly, to empty his low capacity urine reservoir.

The present incontinence device preferably is constructed of heavy duty plastic materials so as to allow the device to be utilized over and over again, saving substantial user dollars each year. It is noted, however, that the user will need to rinse out the device every 24 hours, or so with warm water that has a mix of a mild anti-bacterial soap, and a mild disinfectant. The entire device is designed to be hand washable only, and it is recommended that the entire unit be hand washed at least once a week.

The construction of the brief, and particularly the strap 22, 24 and 26 arrangement, facilitates ease of defecation by not requiring removal of the device, best seen in FIG. 2.

The design and construction of the present device, particularly with the manner in which the brief 14 supports all of the other components, allows the weight of the entire device and its contents to be easily distributed to the user's waist, thighs and hips. There is no weight bearing required by the penis.

The size of the present device is quite similar to a standard man's boxer shorts, such that the area required by the device is relatively small for the same to be concealed and utilized to its fullest potential, and satisfaction.

The device is a self-contained unit with everything being provided and no attachments required. It does not require hooks, rings, adhesive strips, snap fasteners, latches, buzzers, Velcro or other devices to function properly.

The device can be utilized both awake and asleep with total confidence at any time or place.

While embodiments of the present invention have been shown and described, various modifications may be made without departing from the scope of the present invention, and all such modifications and equivalents are intended to be covered.

What is claimed is:

1. A male incontinence device comprising
   a waistband for encircling the waist of a user, and including a plurality of straps for maintaining the waistband in position about the waist of the user, the waistband having a front side to be worn adjacent the abdomen of a user, a reservoir having an upper end securely attached to the front side of the waistband and having a lower end, a condom sheath disposed within an upper end of the reservoir and having at least a portion thereof securely attached to the inside of the front side of the waistband near where the upper end of the reservoir is attached, the condom sheath containing a penis condom which is elongated and has a lower end with an opening, the opening communicating with an opening in the reservoir, and a drain assembly coupled with the lower end of the reservoir and having at least one drain lock for allowing selective draining of the urine in the reservoir.

2. A device as in claim 1 wherein the penis condom includes an upper end having a drawstring and lock assembly for allowing the upper end of the condom to be cinched at the base of a penis and secured comfortably thereto.

3. A device as in claim 1 wherein the opening of the lower end of the condom to the reservoir includes an anti-siphon valve.

4. A device as in claim 1 wherein the drain assembly includes a rotary valve, and the drain assembly has an outlet in the form of a universal adapter which can couple with conventional hospital bed urine containers for draining of the reservoir thereto.

5. A device as in claim 4 wherein a receptacle is provided on an outer surface of the reservoir, and the drain assembly is adapted to be folded to allow an end of the universal adapter to connect with the receptacle to both facilitate preventing accidental draining of the reservoir and for maintaining the drain assembly in a compact manner to be less obtrusive inside a wearer's pants leg.

6. A device as in claim 1 wherein the straps of the waistband and include first and second straps extending downwardly from right and left sides of the waistband and further having lower ends attached to a lower end of a strap loop, the strap loop having upper ends attached to a front portion of the waistband, the waistband and strap assembly serving to maintain the male incontinence device properly oriented on the waist of a male.

7. A device as in claim 6 wherein the condom includes an upper end having a drawstring and lock assembly for allowing the upper end of the condom to be cinched at the base of a penis and secured comfortably thereto.

8. A male incontinence device comprising a waistband for encircling the waist of a user, and including a plurality of straps for maintaining the waistband in position about the waist of the user, a reservoir having an upper end securely attached to a forward side of the waistband, a penis condom disposed within an upper end of the reservoir, the condom being elongated and having a lower end with an opening, the opening communicating with an opening in the reservoir, the penis condom further including an upper end having a drawstring assembly for allowing the upper end of the condom to encircle and be cinched at around the base of a penis and secured thereto; and a drain assembly coupled with the lower end of the reservoir and having at least one drain lock for allowing selective draining of urine in the reservoir.

9. A device as in claim 8 wherein the opening in the lower end of the condom includes an anti-siphon valve.

10. A device as in claim 8 wherein the drain assembly includes a liquid valve and the drain assembly has a universal adapter outlet.

11. A device as in claim 10 wherein a receptacle is provided on an outer surface of the reservoir, and the drain assembly is adapted to be folded to allow an end of the universal adapter to attach to the receptacle to facilitate preventing accidental draining of the reservoir and for maintaining the drain assembly in a compact manner.

12. A male incontinence device comprising a waistband for encircling the waist of the user, and including a plurality of straps for maintaining the waistband in position about the waist of the user, the straps including first and second straps extending downwardly from right and left sides of the waistband and further having lower ends attached to a lower end of a strap loop, the strap loop having upper ends attached to a front portion of the waistband, a reservoir having an upper end securely attached to a forward side of the waistband, a penis condom disposed within an upper end of the reservoir, the condom being elongated and having a lower end with an opening, the opening communicating with an opening in the reservoir, the condom further including an upper end having a drawstring and lock assembly for allowing the upper end of the condom to be cinched at the base of a penis and secured thereto, the opening of the lower end of the condom to the reservoir including an anti-siphon valve, a drain assembly coupled with the lower end of the reservoir and having a rotary valve, and an outlet in the form of a universal adapter which can couple with a conventional hospital bed urine container for draining of the reservoir thereto, and a receptacle on an outer surface of the reservoir, and the drain assembly is adapted to be folded to allow an end of the universal adapter to connect with the receptacle to facilitate preventing accidental draining of the reservoir.

13. A male incontinence device comprising a waistband for encircling the waist of a user and maintaining the waistband in position about the waist of the user, the waistband having a front to be worn adjacent the abdomen of a user, a reservoir having an upper end securely attached to the front of the waistband and having a lower end, a condom sheath disposed within an upper end of the reservoir and having at least a portion thereof securely attached to the inside of the front side of the waistband near where the upper end of the reservoir is attached, the condom sheath containing a penis condom which is elongated and has a lower end with an opening, the opening communicating with an opening in the reservoir, the penis condom further including a flexible upper end having a drawstring and locking device assembly for allowing the upper end of the condom to encircle the base of a penis and be secured thereto, and a drain assembly coupled with the lower end of the reservoir and having at least one drain lock for allowing selective draining of the urine in the reservoir.

14. A device as in claim 13 wherein a portion of the sheath is attached to the inside of the front of the waistband.

15. A device as in claim 13 wherein the condom is approximately 2½ inches wide and approximately seven inches long to accommodate virtually all males.

16. A device as in claim 15 wherein the condom is formed of latex rubber.

17. A device as in claim 13 wherein the drawstring and locking device assembly comprises a drawstring around the upper end of the condom, and the drawstring has ends extending through the locking device to allow the drawstring to cinch the upper end of the condom reasonably tight by pulling the drawstring through the locking device.

18. A device as in claim 13 wherein the opening of the lower end of the condom to the reservoir includes an anti-siphon valve.

19. A device as in claim 13 wherein the drain assembly includes a valve, and the drain assembly has an outlet in the form of a universal adapter which can couple with conventional urine containers for draining of the reservoir thereto.

20. A device as in claim 19 wherein a receptacle is provided on an outer surface of the reservoir, and the drain assembly is adapted to be folded to allow an end of the universal adapter to connect with the receptacle to both facilitate preventing accidental draining of the reservoir and for maintaining the drain assembly in a compact manner to be less obtrusive inside a wearer's pants leg.

21. A device as in claim 13 wherein the waistband includes first and second straps extending downwardly from right and left sides of the waistband and further having lower ends attached to a lower end of a strap loop, the strap loop having upper ends attached to a front portion of the waistband, the waistband and strap assembly serving to maintain the male incontinence device properly oriented on the waist of a male.

22. A male incontinence device comprising a waistband for the waist of a user, the waistband having a front to be worn adjacent the abdomen of a user, a reservoir having an upper end securely attached to the front side of the waistband and having a lower end, a condom sheath disposed within an upper end of the reservoir and having at least a portion thereof securely attached to the waistband near where the upper end of the reservoir is attached, the condom sheath containing a penis condom which is elongated and has a lower end with an opening, the opening communicating with an opening in the reservoir, the penis condom including an upper end having a drawstring and lock assembly for allowing the upper end of the condom to be cinched at and around the base of a penis and secured comfortably thereto, and a drain assembly coupled with the lower end of the reservoir for allowing selective draining of the urine in the reservoir.

23. A device as in claim 22 wherein the opening of the lower end of the condom to the reservoir includes an anti-siphon valve.

24. A device as in claim 22 wherein the waistband includes first and second straps extending downwardly from right and left sides of the waistband and further having lower ends attached to a lower end of a strap loop, the strap loop having upper ends attached to a front portion of the waistband, the waistband and straps serving to maintain the male incontinence device properly oriented on the waist of a male.

25. A device as in claim 22 wherein the condom is formed of latex rubber.

* * * * *